US00PP17882P2

(12) United States Plant Patent
Cornelis

(10) Patent No.: US PP17,882 P2
(45) Date of Patent: Jul. 24, 2007

(54) ***PEPEROMIA* PLANT NAMED 'DAPEP2106'**

(50) Latin Name: *Peperomia obtisufolia*
Varietal Denomination: Dapep2106

(76) Inventor: Daniel Cornelis, Oude Gaverweg 2 B-9820, Melsen-Merelbeke (BE)

( * ) Notice: Subject to any disclaimer, the term of this patent is extended or adjusted under 35 U.S.C. 154(b) by 0 days.

(21) Appl. No.: 11/287,057

(22) Filed: Nov. 25, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell

(57) ABSTRACT

A new cultivar of *Peperomia* plant named 'Dapep2106' that is characterized by an upright habit, large glossy green leaves, a strong stem and a long plant life.

1 Drawing Sheet

Botanical classification: *Peperomia obtisufolia.*
Variety denomination: 'Dapep2106'.

BACKGROUND OF THE INVENTION

The present invention relates to a new and distinct cultivar of *Peperomia* plant botanically known as *Peperomia obtisufolia* and hereinafter referred to by the cultivar name 'Dapep2106'.

'Dapep2106' was discovered as a seedling growing in a bed of *Peperomia.* The exact female and male parents are unknown. The cultivar 'Dapep2106' was selected by the inventor in March of 2003 as a single plant in a cultivated area of Melsen-Merelbeke, Belgium.

Asexual reproduction of the new cultivar 'Dapep2106' by leaf cuttings was first performed in 2003 in Melsen-Merelberke, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Dapep2106'. These traits in combination distinguish 'Dapep2106' as a new and distinct cultivar.

1. *Peperomia* 'Dapep2106' exhibits an upright habit.
2. *Peperomia* 'Dapep2106' exhibits large glossy green leaves.
3. *Peperomia* 'Dapep2106' exhibits a strong stem.
4. *Peperomia* 'Dapep2106' exhibits a long plant life.

The closest comparison cultivar are plants of the *Peperomia obtisufolia* species. 'Dapep2106' is distinguishable from plants of the *Peperomia obtisufolia* species by the following characteristics:

1. 'Dapep2106' has larger leaves.
2. 'Dapep2106' has a longer plant life.
3. 'Dapep2106' has glossier leaves.
4. 'Dapep2106' has an upright habit.
5. 'Dapep2106' has a stronger stem.

BRIEF DESCRIPTION OF THE DRAWING

The accompanying photograph illustrates the distinguishing traits of *Peperomia* 'Dapep2106'. The plant in the photograph shows an overall view of a 6 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Peperomia* cultivar named 'Dapep2106'. Data was collected in Melsen-Merelbeke, Belgium from 6 month old glass greenhouse grown plants in 17 cm. containers. The time of year was Summer and the average daytime and nighttime temperatures were 19° Centigrade. The light level was natural outdoor light and there were no photoperiodic treatments. Color determinations are in accordance with The Royal Horticultural Society Colour Chart 2001 edition, except where general color terms of ordinary dictionary significance are used. The growing requirements are similar to the species. 'Dapep2106' has not been tested under all possible conditions and phenotypic differences may be observed with variations in environmental, climatic, and cultural conditions, however, without any variance in genotype.

Botanical classification: *Peperomia obtisufolia* 'Dapep2106'.
Use: Ornamental Perennial.
Parentage: The parents of 'Dapep2106' are unknown.
Vigor: Moderate.
Growth rate: Approximately 12 cm. per month.
Growth habit: Narrow upright.
Plant shape: Inverted triangle.
Suitable container size: 10.5 cm. container.
Height: Average 59.0 cm. in height.
Width: Average 35.6 cm. in width.
Hardiness: Zone 10.
Propagation: Cuttings.
Time to initiate roots: Approximately 21-28 days to produce roots on an initial cutting.
Time to produce a rooted cutting or liner: Approximately 56 days.
Root system: Fine and fibrous.

Stem:
*Branching habit.*—Moderate.
*Average number of lateral branches:* 6.
*Pinching.*—No.
*Lateral branch diameter.*—1.0 cm. in diameter.
*Lateral branch length.*—30.2 cm. in length.
*Lateral branch color.*—143A to 144A.
*Lateral branch strength.*—Strong.
*Stem color.*—143A to 144A.
*Pubescence.*—Absent.
*Internode length.*—5.6 cm. between nodes.
*Shape.*—Rounded.
*Surface.*—Glossy.
*Stem strength.*—Strong.

Foliage:
*Texture.*—Glossy.
*Leaf arrangement.*—Alternate.
*Compound or single.*—Single.
*Quantity of leaves per lateral branch.*—7.
*Leaf shape.*—Cordate.
*Leaf apex.*—Apiculate.
*Leaf base.*—Cordate.
*Leaf length.*—13.5 cm. in length.
*Leaf width.*—12.2 cm. in width.
*Pubescence.*—Absent.
*Leaf margin.*—Entire.
*Vein pattern.*—Camptodrome.
*Young leaf color* (*upper surface*).—143A.
*Young leaf color* (*lower surface*).—143C to 144A.
*Mature leaf color* (*upper surface*).—139A.
*Mature leaf color* (*lower surface*).—146B.
*Vein color* (*lower surface*).—146B.
*Vein color* (*upper surface*).—144A to 144B.
*Leaf attachment.*—Petiolate.
*Petiole dimensions.*—8.1 cm. in length and 4.5 mm. in diameter.
*Petiole color.*—144A.
*Durability of foliage to stress.*—Moderate.

Flower:
*Flower arrangement.*—Stalked terminal spikes.
*Inflorescence type.*—Spike.
*Inflorescence dimensions.*—16.8 cm. in diameter and 15.9 cm. in height.
*Flowering habit.*—Continuously.
*Quantity of spikes per inflorescence.*—Approximately 10.
*Quantity of flowers per spike.*—Approximately 1500.
*Quantity of flower buds per spike.*—Approximately 1500.
*Quantity of flowers and buds per plant.*—Approximately 75,000.
*Flowering season.*—Autumn.
*Rate of flower opening.*—Approximately 75% of the flowers are opened at one stage.
*Fragrance.*—None.
*Flower bud length.*—0.5 mm. in length.
*Flower bud diameter.*—0.5 mm. in diameter.
*Flower bud shape.*—Flattened.
*Bud color.*—193A.
*Rate of bud opening.*—2 days per bud, 7 days per spike.
*Flower aspect.*—Upright to slightly outward.
*Flower shape.*—Individual flowers consist of two stamens fused to form a single anther and a single pistil.
*Flower dimensions.*—Average 0.7 mm. in diameter and 0.3 mm. in height.
*Flower longevity.*—Lasts approximately 14 days on plant.
*Self-cleaning or persistent.*—Persistent.
*Bracts.*—Absent.

Peduncle:
*Peduncle length.*—7.7 cm.
*Peduncle diameter.*—4 mm.
*Peduncle angle.*—30° from vertical.
*Peduncle strength.*—Moderate.
*Peduncle color.*—152A to 152B.

Pedicels:
*Pedicel length.*—4.5 mm.
*Pedicel diameter.*—3 mm.
*Pedicel angle.*—30° from vertical.
*Pedicel strength.*—Moderately weak.
*Pedicel color.*—143B.

Reproductive organs:
*Stamen number.*—2 stamen fused into one anther.
*Anther shape.*—Kidney shaped.
*Anther size.*—0.3 mm in length.
*Anther color.*—161D.
*Amount of pollen.*—High.
*Pollen color.*—157A.
*Pistil number.*—1.
*Pistil dimensions.*—1.1 mm. in length.
*Stigma shape.*—Clavate.
*Stigma color.*—192C.
*Style length.*—0.2 mm.
*Style color.*—192C.
*Ovary color.*—192C.

Seed: Seed production has not been observed.

Disease and pest resistance: Plants of the new *Peperomia* have not been observed for disease or pest resistance.

It is claimed:

1. A new and distinct variety of *Peperomia* plant named 'Dapep2106' as described and illustrated.

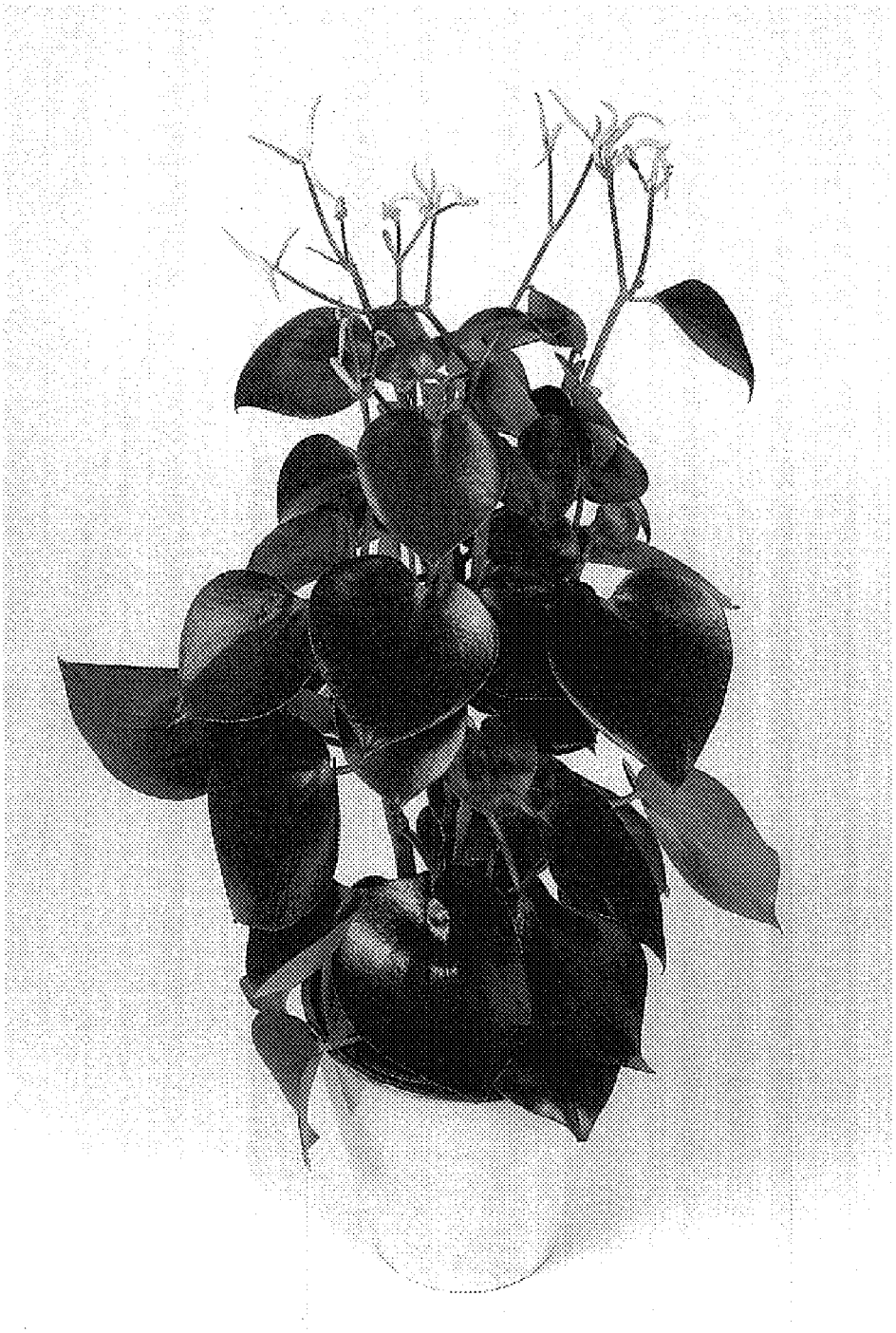

* * * * *